United States Patent

Ohmi et al.

[11] Patent Number: 5,578,833
[45] Date of Patent: Nov. 26, 1996

[54] ANALYZER

[75] Inventors: Tadahiro Ohmi, 1-17-301, Komegabukuro 2-chome, Aoba-ku, Sendai-shi, Miyagi-ken 980; Koji Kotani, Miyagi-ken, both of Japan

[73] Assignee: Tadahiro Ohmi, Sendai, Japan

[21] Appl. No.: 211,381

[22] PCT Filed: Oct. 1, 1992

[86] PCT No.: PCT/JP92/01265

§ 371 Date: Apr. 25, 1994

§ 102(e) Date: Apr. 25, 1994

[87] PCT Pub. No.: WO93/07470

PCT Pub. Date: Apr. 15, 1993

[30] Foreign Application Priority Data

Oct. 1, 1991 [JP] Japan .................. 3-280417

[51] Int. Cl.[6] .................................. G01N 21/64
[52] U.S. Cl. ..................... 250/461.1; 250/358.1; 250/360.1
[58] Field of Search ................. 250/372, 458.1, 250/461.1, 572, 358.1, 359.1, 360.1; 356/237

[56] References Cited

FOREIGN PATENT DOCUMENTS

| | | |
|---|---|---|
| 63-168520 | 7/1963 | Japan . |
| 58-210551 | 12/1983 | Japan . |
| 61-182238 | 8/1986 | Japan . |
| 61-296204 | 12/1986 | Japan .................. 250/458.1 |
| 62-159028 | 7/1987 | Japan . |
| 62-269048 | 11/1987 | Japan .................. 250/458.1 |
| 63-103951 | 5/1988 | Japan . |
| 1-102342 | 4/1989 | Japan . |
| 1-148946 | 6/1989 | Japan .................. 250/458.1 |
| 2-307164 | 12/1990 | Japan . |
| 2-309206 | 12/1990 | Japan .................. 250/458.1 |

OTHER PUBLICATIONS

Inman et al., "Development of a Pulsed–Laser, Fiber Optic Based Fluorimeter: Determination of Fluorescence Decay Times of Polycyclic Aromatic Hydrocarbons in Sea Water", Analytica Chimica Acta, 239 (1990), pp. 45–51.

Primary Examiner—Carolyn E. Fields
Assistant Examiner—Edward J. Glick
Attorney, Agent, or Firm—Baker & Daniels

[57] ABSTRACT

An analyzer capable of detecting a light element, such as Na, capable of evaluating a sample having an uneven surface, such as a pattern-carrying wafer without destroying and damaging the same. The analyzer is of simple construction, is simple in operation, is safe for the human body, and is capable of identifying the composition of a minute amount of impurities and fine particles deposited on the surface of a sample. The analyzer has a sample retaining stage, an ultraviolet ray-emitting light source, a collector for collecting the ultraviolet rays generated by the light source and for applying the resultant rays to the surface of a sample, and a detector for detecting the light emitted from the surface of the sample to which the ultraviolet rays have been applied.

19 Claims, 6 Drawing Sheets

ANALYZER

TECHNICAL FIELD

The present invention relates to an analyzer. More specifically it relates to an analyzer which is capable of the analysis of minute amounts of impurities on a surface.

BACKGROUND ART

Total reflection fluorescence X-ray analyzers and surface particle detectors are commonly known as analyzers which conduct the evaluation of minute amounts of impurities or particles on a sample surface, for example a wafer surface.

The former is an analyzer which employs X rays and evaluates the minute amounts of heavy metal impurity contamination on a sample surface, while the latter is an evaluator for detecting fine particles deposited on a sample surface using, for example, a laser beam.

Figure 16:
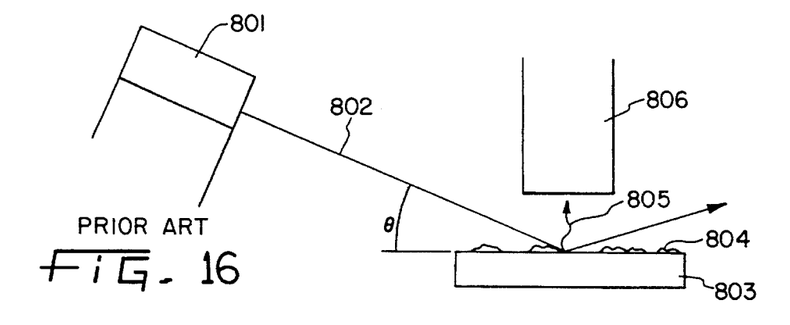
FIG. 16 is a conceptual diagram of a conventional total reflection fluorescence X ray analyzer.

Using FIG. 16 below, a conventional total reflection fluorescence X-ray analyzer will be explained. In FIG. 16, reference 801 indicates an X ray source, and the X ray 802 generated therein is applied to sample 803 at an angle of incidence θ which fulfills total reflection conditions (for example, θ=0.05 degrees). As a result of the application of this X ray 802, fluorescence X rays 805 are emitted from impurity substances 804 deposited on the surface of sample 803. These are detected by X ray detector 806. These fluorescence X rays 805 have a wavelength (energy) specific to the contaminant substances 804, so that it is possible to determine the contaminant substances, and furthermore, it is possible to evaluate the degree of contamination from the strength of the fluorescence X rays 805.

Figure 17:
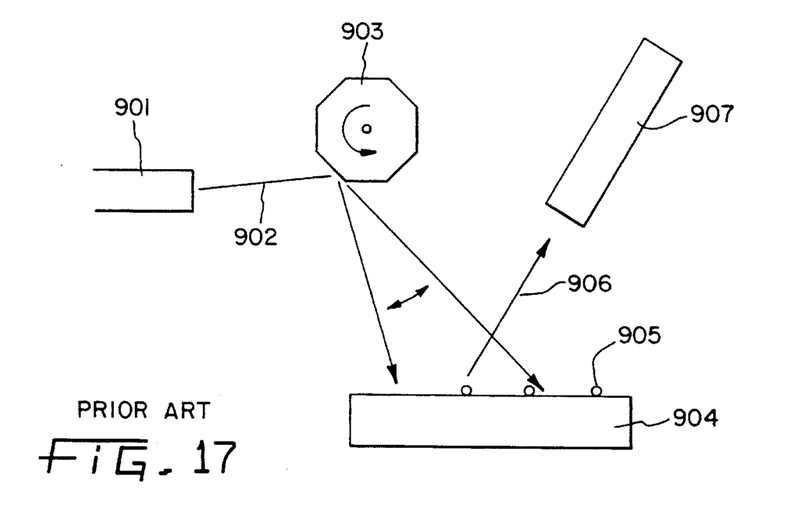
FIG. 17 is a conceptual diagram of a conventional surface particle detector.

Next, using FIG. 17, a conventional surface particle detector will be explained. In FIG. 17, Ref. 901 indicates a laser beam source, and the laser beam 902 generated therein scans the surface of a sample 904 by means of a light scanner 903 comprising, for example, a rotating polygonal mirror. If fine particles 905 have been deposited on the surface of sample 904, then the laser beam 902 will be irregularly reflected by fine particles 905, and the irregularly reflected light 906 will be detected by light detector 907, and the detection and evaluation of fine particles 905 thus conducted.

However, in the conventional apparatuses described above, the following problems are present. In the total reflection fluorescence X ray analyzer, the detection of heavy metals such as copper (Cu), iron (Fe), chromium (Cr), and the like, is possible; however, it is impossible to detect sodium (Na) or carbon (C), which constitute extremely important impurities in semiconductor processes. That is to say, there are limitations in the elements which are detectable. Furthermore, X rays are employed, so that some damage is caused to the samples. More concretely, in a Si substrate, or at the Si—SiO$_2$ boundary, the bonds between atoms are broken, so that it is impossible to employ such an apparatus in the analysis of wafers during the manufacturing of devices. Furthermore, because X rays are employed, some danger is posed to the human body, and the X ray optical system and the detector are structurally complex. Furthermore, it is necessary to constantly conduct the liquid nitrogen cooling of the fluorescence X ray detector, so that the operation thereof is quite complex and difficult. On the other hand, in a surface particle detector, because the detection of light which is irregularly reflected by means of particles is carried out, testing using samples having irregularities other than deposited particles, such as pattern carrying wafers or the like, is impossible. Furthermore, there are problems in that the determination of the components of the deposited particles is impossible, and the like.

The present invention has as an object thereof to provide an analyzer capable of detecting light elements such as Na or the like, capable of evaluating samples having uneven surfaces, such as pattern carrying wafers or the like, without destroying or causing damage to the sample, having a simple composition and simple operation, and which is safe to the human body, and which is capable of identifying the composition of minute amounts of impurities or fine particles deposited on the surface of a sample.

SUMMARY OF THE INVENTION

The analyzer of the present invention is characterized in being provided with a sample retaining stage, an ultraviolet ray-emitting light source, a means for collecting the ultraviolet rays sent out from the light source and applying the resultant rays to the surface of a sample, and a means for detecting the light emitted from the surface of the sample to which the ultraviolet rays have been applied.

In the present invention, ultraviolet rays are used as the applied light, and the fluorescent light emitted by the surface of the sample is detected, and thereby, it is possible to detect light elements such as Na or the like, without destroying or causing damage to the sample, while having a simple composition and operation, and being safe to the human body. Accordingly, it is possible to simply and rapidly conduct a surface analysis without the necessity of a complicated operation. Furthermore, by observing the wavelength distribution and strength of the fluorescent light emitted by the surface of the sample, it is possible to identify the composition of the minute amounts of impurities or fine particles deposited on the surface of the sample, or to measure the degree of contamination.

DESCRIPTION OF THE REFERENCES 101 ultraviolet ray source (mercury lamp), 102 ultraviolet ray, 103 light-gathering instrument (optical lens), 104 sample (Si wafer), 105 impurities, 106 fluorescent light, 107 spectrograph (diffraction grating), 108 light detector (photo diode detector), 109 sample stage, 201 spectroscope, 202 fluorescent light, 203 light amplifying detector (photo multiplier), 301 spectroscope, 302 fluorescent light, 303 detector, 401 ultraviolet ray light source, 402 ultraviolet ray, 403 light-gathering instrument, 404 light scanner, 405 sample, 406 impurities, 407 fluorescent light, 501 sample, 502 stage, 503 stage drive mechanism, 601 ultraviolet ray light source, 602 light-gathering instrument, 603 diffraction grating spectrograph, 604 aperture, 605 monochromatic ultraviolet ray, 606 sample, 701 mercury lamp, 702 ultraviolet ray, 703 light-gathering instrument, 704 polarizer, 705 singly polarized ultraviolet ray, 706 sample, 801 X ray source, 802 X ray, 803 sample, 804 contaminating substance, 805 fluorescence X ray, 901 laser beam source, 902 laser beam, 903 light scanner, 904 sample, 906 irregularly reflected light, 907 light detector.

BEST MODE FOR CARRYING OUT THE INVENTION (Embodiment 1)

A first embodiment of the present invention will be explained with reference to FIG. 1.

Figure 1:
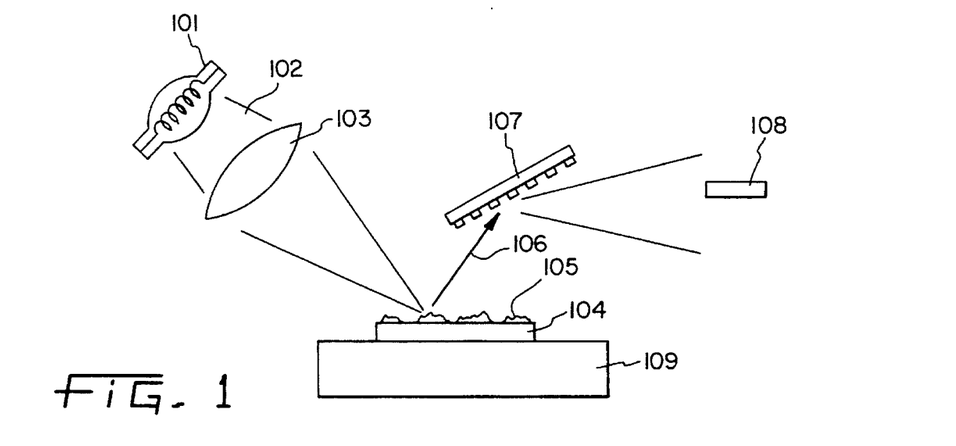
FIG. 1 is a conceptual diagram showing an analyzer in accordance with a first embodiment.

FIG. 1 is a conceptual diagram of the apparatus. In this apparatus, an ultraviolet ray 102 emitted by an ultraviolet ray light source 101, for example, a mercury lamp, is collected in a light-gathering instrument 103, for example an optical lens, and is applied to the surface of the sample 104, for example, an Si wafer, which is retained on a sample stage 109. Fluorescent light 106 having a wavelength corresponding to Si and to the type of metallic impurity elements is emitted from the Si wafer surface and from the impurities 105, such as metallic elements and the like, deposited on the surface of the Si wafer. Among the fluorescent light 106, that portion which is visible is divided into its spectra by spectroscope 107, for example, a diffraction grating and is introduced into light detector 108, for example, a photo diode detector. By altering the position of the photo diode detector, it is possible to discriminate the wavelengths of the light contained in fluorescent light 106. There is a 1 to 1 correspondence between the wavelengths of this light and the types of impurity elements, so that it is possible to identify the impurity elements. Furthermore, by means of the strength of the light detected by means of light detector 108, it is possible to estimate the amounts of the impurity elements.

Hereinbelow, the characteristics of the apparatus of the present invention and the striking effects obtained thereby will be explained. The first characteristic is the use of ultraviolet rays as the applied light. In comparison with cases in which X rays were employed as the applied light, as in conventional analyzers, there is no danger of destroying or causing damage to the sample, and the danger to the human body is greatly reduced, and the apparatus itself also becomes simpler. Accordingly, it becomes possible to conduct the inspection of wafers during processing on a semiconductor manufacturing line easily and at a high throughput rate.

A second characteristic feature is the detection, by means of light detector 108, of only the visible component of the fluorescent light which is emitted from the surface of sample 104 and the impurities 105 which are deposited on the surface of the sample 104. In comparison with the case in which fluorescence X rays were detected, as in conventional analyzers, the detector itself can be simply achieved, and complicated operations such as constant cooling using liquid nitrogen can be omitted, so that the apparatus itself becomes simple and the operation thereof becomes extremely easy. Furthermore, it becomes possible to detect light elements such as Na and the like which could not be detected by means of conventional analyzers. In addition, the optical system containing a light instrument such as a lens or the like for the detection of light, does not require special materials, and technology which was conventionally developed in the field of photographic technology can be employed, so that design and operation of the apparatus are extremely simple.

A third characteristic feature is that the spectroscope 107 is disposed in front of the light detector 108. By means of the spectroscope 107 and the moveable light detector 108, it is possible to observe the wavelength distribution (spectra) of the fluorescent light emitted by the surface of the sample 104 and the impurities 105 deposited on the surface of the sample 104, and it thus becomes possible to identify the chemical composition, that is to say, the component elements of a sample 104 and of impurities 105 deposited on the surface of the sample 104, which was not previously known.

Figure 2:
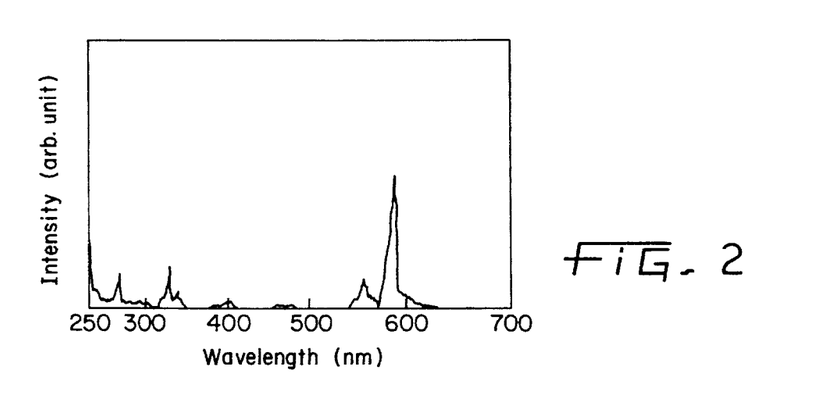
FIG. 2 is a diagram showing the fluorescence spectrum of the element Na as detected by means of the apparatus of the present invention.

In FIG. 2, the fluorescence spectra of the element Na as detected by the apparatus of the present invention are shown. A Si wafer which was immersed in ultrapure water into which 1 ppb of Na had been intentionally mixed, and which was then desiccated, was used as the sample. A large peak resulting from the fluorescent light of Na was observed in the vicinity of a wavelength of 589 nm. It was determined from the peak strength that the contamination concentration of Na on the surface of the Si wafer was $8 \times 10^{11}$ atoms/cm$^2$.

Figure 3:
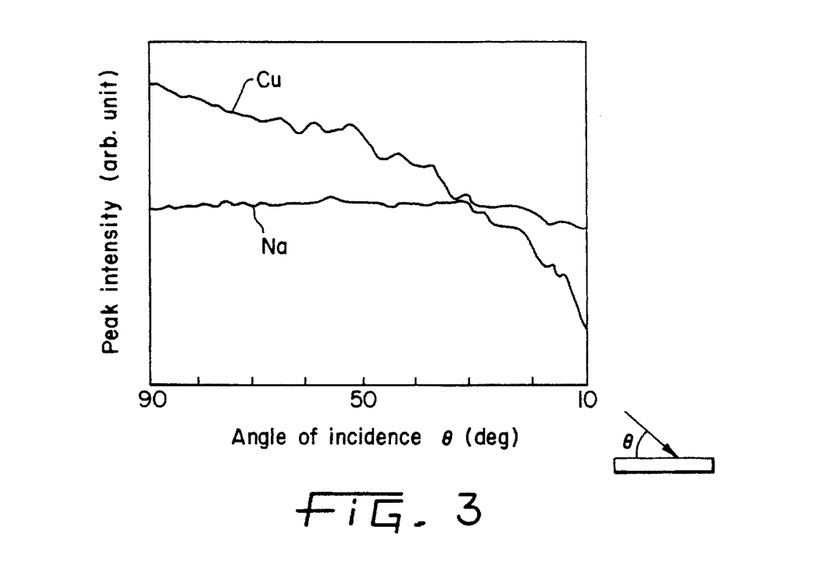
FIG. 3 is a diagram showing an example of the measurement of the distribution in the direction of depth.
Figure 4:
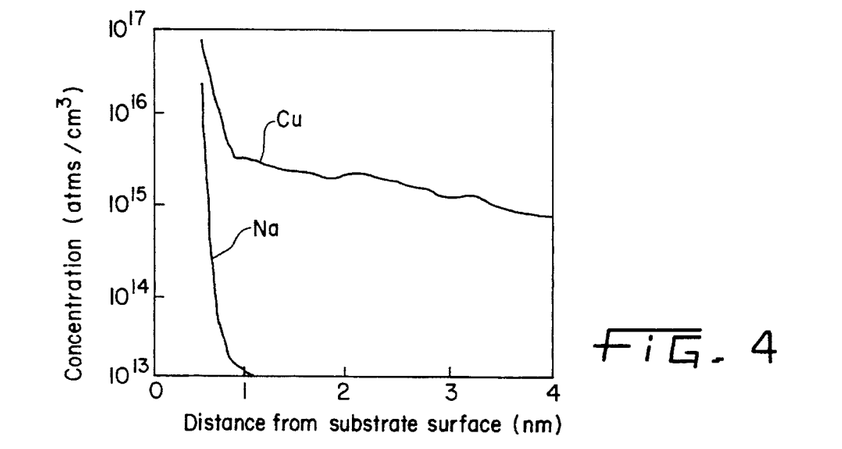
FIG. 4 is a diagram showing the dependence on the angle of ultraviolet ray incidence of peak strength, as a density distribution in the direction of depth.

Furthermore, it has become clear that it is possible to alter the range in the direction of the depth of the analysis region of the sample, and to obtain a distribution in the direction of depth of the components which are the object of the analysis, by either making the ultraviolet application part comprising the ultraviolet ray light source 101 and the light-gathering instrument 103 movable, or making the angle of the sample stage 109 with respect to the ultraviolet ray application part variable, in order to alter the angle of incidence at which the ultraviolet ray is applied to the sample 104. That is to say, as the angle of incidence θ becomes smaller, the depth of incidence of the ultraviolet ray is reduced. In FIG. 3, an example of the measurement of the distribution in the direction of depth is shown. The sample was a quartz substrate, in the examples in which the substrate was immersed in ultrapure water into which 100 ppb of Na or Cu had been blended and was thus intentionally contaminated. The peak strength of Na was essentially constant even when the angle of incidence was reduced, and it was thus determined that only Na was present on the surface. On the on the other hand, in the case of Cu, as the angle of incidence was reduced, the peak strength also decreased. This indicated that Cu was also present in the interior of the Si wafer. The data regarding the dependence of peak strength on the angle of ultraviolet ray incidence was processed by means of a computer, and an example in which this was outputted as a concentration distribution in the direction of depth is shown in FIG. 4.

Figure 5:
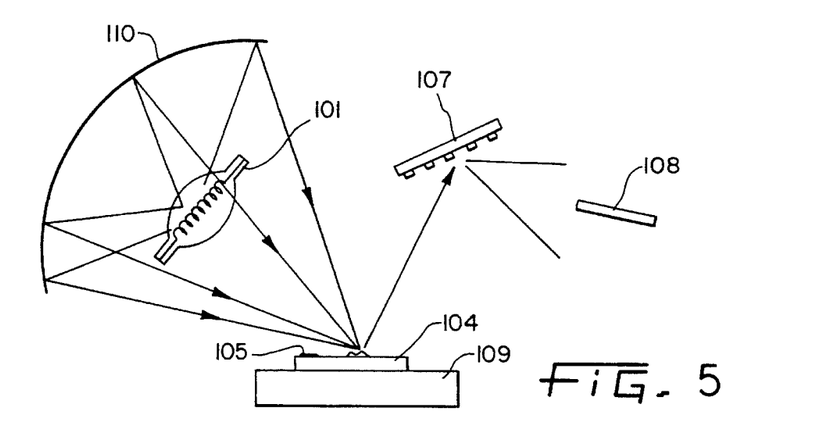
FIG. 5 is a conceptual diagram showing an example using a concave mirror in the first embodiment.

In the present embodiment an example was employed in which a mercury lamp was used as ultraviolet ray source 101; however, other sources may be employed in so far as there are light sources which emit ultraviolet rays; for example, a deuterium lamp may be employed. An ekishima laser may be used as the light source, and in this case, the light-gathering instrument 103 may be omitted. Furthermore, an example was explained in which an optical lens was employed as the light-gathering instrument 103; however, any apparatus may be employed in so far as it acts as a light-gathering instrument, for example, a concave mirror may be employed. An embodiment in which a concave mirror 110 was employed was shown in FIG. 5. A Si wafer is used as an example of sample 104; however, it is of course the case that this sample is in no way limited to a Si wafer. An example was explained in which a diffraction grating was employed as spectrograph 107; however, other apparatuses may be employed in so far as they act to separate light, for example, a prism may be employed. An example was used in which a photo diode was employed as light detector 108; however, other apparatuses may be employed in so far as they act to detect light. An example was used in which the light detector 108 was movable; however, even if the light detector 108 is fixed, it is of course the case that the detection of known single elements and the measurement of surface concentration are possible. In addition, the explanation was conducted using an apparatus in which the fluorescent light detector comprised a spectroscope 107 and a light detector 108; however, even if the fluorescent light detector comprises an apparatus comprising 1 or a plurality of interchangeable filters transmitting light having specified wave lengths and a light detector, it is expected that the striking effects described in the present embodiment will be achieved.

In the present embodiment, only the case in which light within the visible range was detected was explained; however, it is of course the case that the apparatus is not restricted only to visible light. Light having a great variety of wavelengths is contained in fluorescent light, and it is also effective to analyze, for example, ultraviolet light or infrared light. For example, in the case in which ultraviolet light is employed, it is preferable to use a material which does not absorb ultraviolet light in the lens (for example, quartzite or synthetic quartz). As a result of this type of analysis, it is possible to conduct a more detailed analysis of impurities.

(Embodiment 2)

A second embodiment of the present invention will be explained using FIG. 6.

Figure 6:
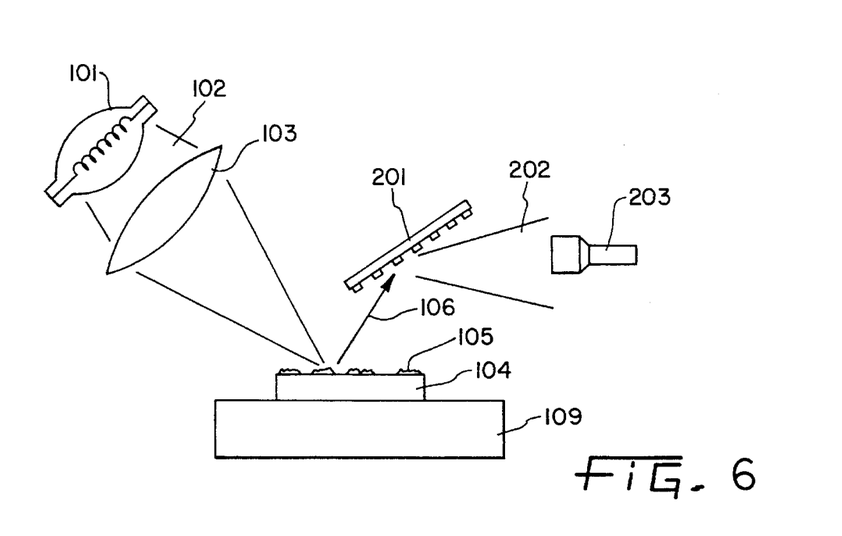
FIG. 6 is a conceptual diagram of an analyzer in accordance with the second embodiment.

FIG. 6 is a conceptual diagram of the present apparatus. In the fluorescent light detector, ultraviolet light 202 separated by means of a spectroscope 201, for example, a diffraction grating, is introduced into a light amplifying detector 203, for example, a photo multiplier, and is detected. The photo multiplier comprises a photo electric plate cathode comprising cesium, antimony, or the like, at least 1 secondary electron emission plate comprising beryllium copper or the like, to which a high voltage is applied, and an anode which detects electrons. When the photoelectric plate cathode receives light, it emits electrons as a result of the photoelectric effect. The electrons which are thus emitted are accelerated in a strong electric field, and are applied to the secondary electron emission plate. At this time, a plurality of electrons are emitted from the secondary electron emission plate. In addition, the electrons thus emitted are accelerated by the strong electric field applied between this secondary emission plate and the next secondary electron emission plate, are applied to the next secondary electron emission plate, and a further plurality of electrons are produced. This process is repeated, an extremely large number of electrons are produced from very weak light, and this is detected by the anode as an electric current. In the present embodiment, a photomultiplier using a photoelectric plate cathode comprising cesium and line-type secondary electron emission plates, was adopted. The rest of the details of the construction of the apparatus were identical to those described in FIG. 1, so that an explanation thereof is omitted here.

As a result of adopting a photomultiplier as a necessary structural element of the fluorescent light detector, the detection sensitivity is greatly increased; in the detection of Na, in comparison with the case in which a photomultiplier was not used, in which the lower limit of detection was $1 \times 10^{10}$ atms/cm$^2$, when a photomultiplier was employed, it was possible to lower the lower limit of detection by 1 or 2 decimal places.

In the present embodiment, a photomultiplier using a photoelectric plate cathode comprising cesium and line-type secondary electron emission plates was used as the photomultiplier; however, it is possible to use a photomultiplier in which the photoelectric plate comprises antimony, or a photomultiplier using venetian blind-type or box-and-grid-type secondary electron emission plates. In addition, an example was used in which a photomultiplier was employed as the light amplifying detector 203; however, other apparatuses may be employed in so far as they act so as to amplify and detect light, for example, an apparatus comprising a micro channel plate, a fluorescent screen, and a photo diode detector, in which a fluorescent screen is disposed at the anode portion of the photomultiplier, electrons are converted into light, and this light is then detected by a light detector, may also be employed.

Furthermore, an explanation was conducted using an apparatus in which the fluorescent light detector comprised a spectroscope 201 and a light amplifying detector 203; however, the striking effects described in the present embodiment would be expected if an apparatus was employed in which the fluorescent light detector comprised 1 or a plurality of interchangeable filters allowing the transmission of light having specified wave lengths and a light amplifying detector.

(Embodiment 3)

Figure 7:
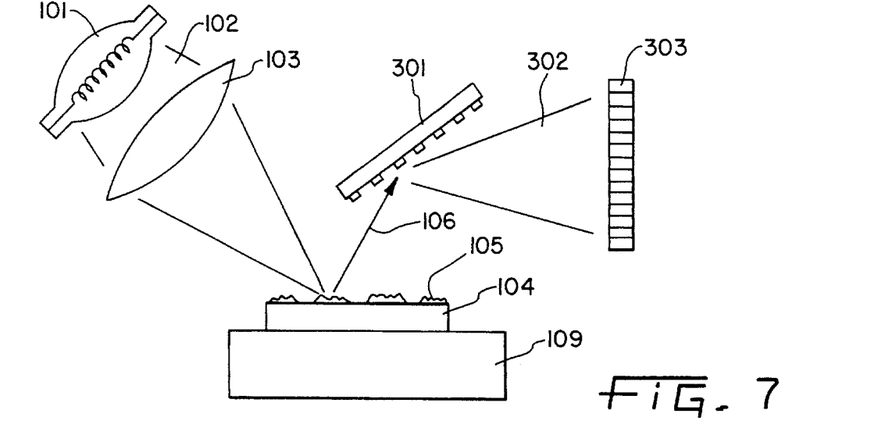
FIG. 7 is a conceptual diagram of an analyzer in accordance with the third embodiment.

A third embodiment of the present invention will be explained using FIG. 7. Fluorescent ray 302 separated by means of spectroscope 301 is detected by means of a plurality of light detectors 303, for example, CCD line sensors, disposed so as to form a series. The other details of the construction are identical to those described in the case of FIG. 1, so that an explanation thereof is omitted here.

By employing CCD line sensors, it becomes possible to instantly measure the wavelength distribution (spectra) of the fluorescent light 302 separated by means of spectroscope 301, and in comparison with the conventional case in which CCD line sensors were not employed, in which the measurement of fluorescent light, having a wavelength within a range of 250 nm to 800 nm, required between 5 and 6 minutes when CCD line sensors were employed, this measurement can be conducted in approximately 2 seconds, so that the measurement period can be greatly shortened. As a result of this, the in-situ continuous measurement of samples, the chemical composition of the surfaces of which samples varied rapidly, which was not conventionally possible, has become possible.

Figure 8:
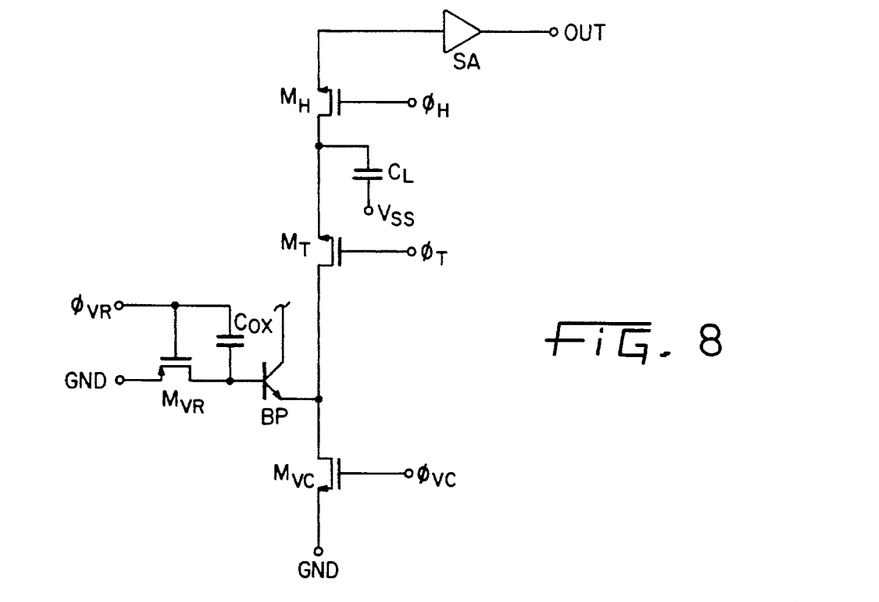
FIG. 8 is a diagram showing an example of an BASIS type sensor.

In the present embodiment, an example was used in which a CCD sensor was employed as the plurality of light sensors 303 arranged in a series; however, any apparatus may be employed in so far as it has a composition in which a plurality of light detectors are disposed so as to form a series. If a BASIS type line sensor, which is a light sensor which is highly resistant to static, since the detector itself acts to amplify a signal, is employed, then the detection sensitivity is increased, and it is of course the case that even very weak light becomes detectable. An example employing BASIS type sensors is shown in FIG. 8. These sensors correspond to each pictured element.

The explanation was conducted using an apparatus in which the fluorescent light detector comprised a spectroscope 301 and a plurality of light detectors 303 arranged so as to form a series; however, the striking effects described in the present embodiment would be obtainable even in an apparatus in which the fluorescent light detector comprised a plurality of groups of filters, allowing the transmission of light having specified wavelengths, and detectors. Furthermore, it is of course the case that the detection sensitivity increases greatly if a light amplifier is disposed before each of the plurality of light detectors.

(Embodiment 4)

Figure 9:
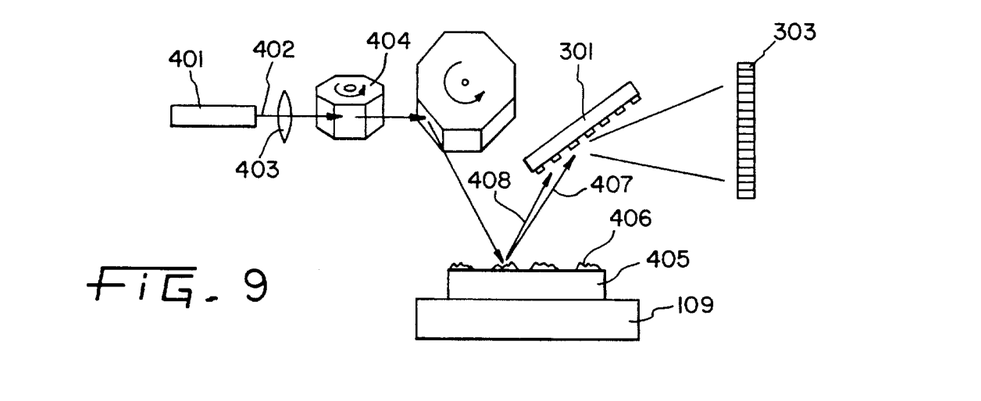
FIG. 9 is a concept diagram of an analyzer in accordance with the fourth embodiment.

A fourth embodiment of the present invention will be explained using FIG. 9. An ultraviolet ray 402 emitted by an ultraviolet ray source 401, for example, an ekishima laser, is collected in a light-gathering instrument 403, for example, an optical lens, is inputted into light scanner 404, for example, 2 rotating polygonal mirrors disposed so that the axes thereof form an angle of approximately 90 degrees with respect to one another, and is thus able to scan the surface of sample 405 in a 2 dimensional manner. With respect to the first light detector, which detects the fluorescent light 407 emitted by sample 405 and the impurities 406 deposited on the surface of sample 405, this is identical to that explained in the third embodiment of FIG. 7, so that an explanation thereof will be omitted here. All other details of the construction are identical to those explained in FIG. 1, so that an explanation thereof will also be omitted here.

Figure 10A:
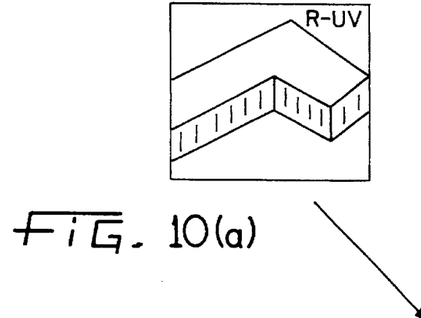
FIGS. 10a, b, and c are diagrams showing the state of the image synthesis processing in the fourth embodiment.
Figure 10B:
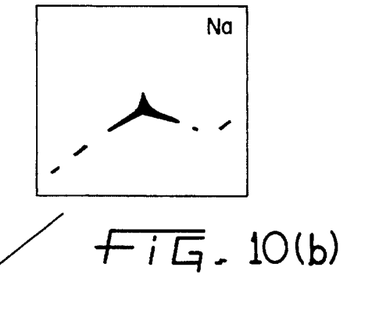
Figure 10C:
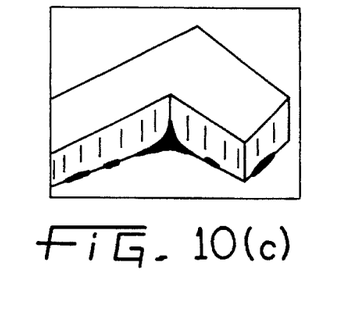

As a result of scanning ultraviolet ray 402 by means of light scanner 404, the distribution of the components which are the object of the analysis on the surface of the sample can be rapidly measured. In addition, by processing a detection signal of (irregularly) reflected ultraviolet light 408 emitted by sample 405 and the impurities 406 deposited on the surface of sample 405, it is possible to display the shape of the surface of the sample on a screen. Furthermore, by means of the detection of fluorescent light 407 after the separation thereof, the signals from the specified components of sample 405 can be separated and extracted, formed into an image by means of signal processing, and then synthesized into an image of the shape of the surface of the sample, and thereby, it becomes possible to observe the state of the localization of specified components resulting from the shape of the surface of the sample as an image. The state of the processing of this image synthesis is shown as a model in FIGS. 10(a–c). FIG. 10(a) shows the image obtained from an irregularly reflected ultraviolet ray. FIG. 10(b) shows the image obtained from Na fluorescent light. FIG. 10(c) shows the synthesized image of localization state of Na. It is clear from FIGS. 10(a–c) that Na tends to segregate in the corner portions of the pattern on the Si wafer.

In the present embodiment, an example was used in which 2 rotating polygonal mirrors which were disposed so that axis thereof formed an angle of approximately 90 degrees with respect to one another were used as light scanner 404; however, other apparatuses may be employed insofar as they permit the scanning of ultraviolet rays on the surface of a sample, for example, 2 movable mirrors which have an oscillation function and which are disposed so that the oscillating axes thereof form an angle of approximately 90 degrees with respect to one another may also be employed. An example was used in which an ekishima laser was employed as ultraviolet ray light source 401; however, other apparatuses may be employed insofar as they constitute ultraviolet ray sources, for example, a deuterium lamp or mercury lamp may also be employed. An example was used in which an optical lens was employed as light-gathering instrument 403; however, other apparatuses may be employed insofar as they act as collectors, for example, a concave mirror may be employed. Furthermore, an image of the sample was synthesized using reflected light; however, if the object of the analysis is the composition of Si or the like, fluorescent light may also be employed for this purpose.

(Embodiment 5)

Figure 11:
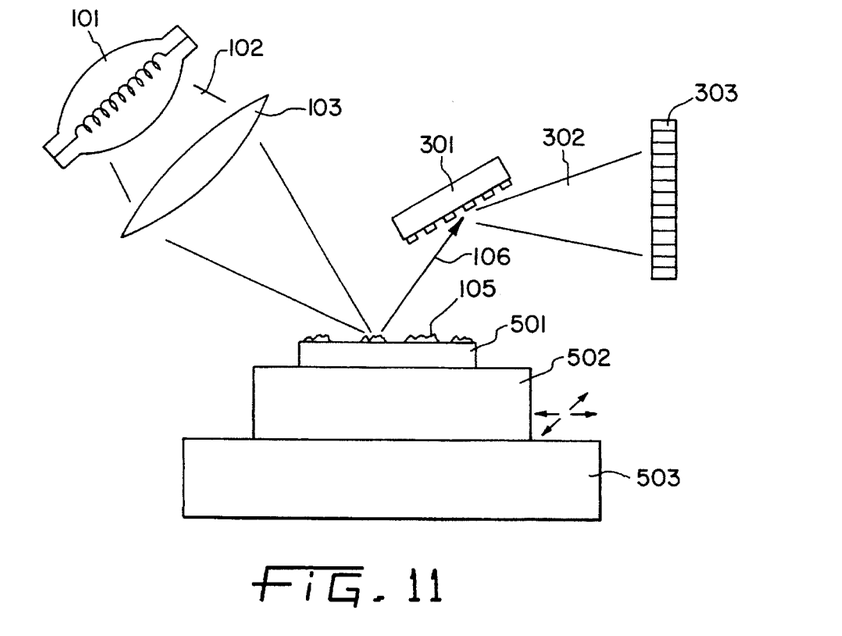
FIG. 11 is a conceptual diagram of an analyzer in accordance with a fifth embodiment.

FIG. 11 shows a fifth embodiment of the present invention. It is characteristic in the present embodiment that a stage driving mechanism 503 which is capable of scanning stage 502, for example, an XY stage driven by a stepping motor, is provided in stage 502 which retains a sample 501. With respect to the ultraviolet ray emitter and the fluorescent light detector, these are identical to those described in the third embodiment of FIG. 7, so that an explanation thereof will be omitted here.

Figure 12:
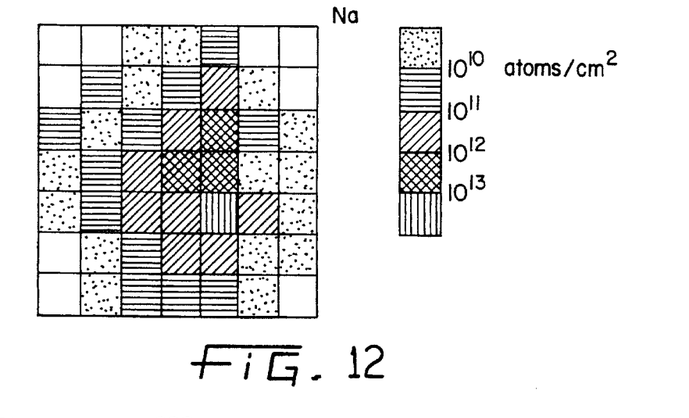
FIG. 12 is a diagram showing an example of the measurement of the Na distribution on a 5 inch Si wafer.

As a result of driving the stage 502 retaining the sample 501 by means of an XY stage driven by a stepping motor, it is possible to scan the incidented ultraviolet ray over a wide region of the surface of sample 501, and it thus becomes possible to measure the concentration on the surface of the sample of the components which are the object of the analysis over a wide region. In FIG. 12, an example of the measurement of the distribution of Na on a 5 inch silicon wafer is shown. By displaying the strength of the detected Na concentration on screen in terms of color or shades of grey it is possible to determine where the Na is distributed on the Si wafer, and to what degree. In addition, as a result of using an ultraviolet ray emitter incorporating the light scanner 404 described in the fourth embodiment as the ultraviolet ray emitter, it is possible to realize both the scanning of the ultraviolet ray by means of light scanner 404 and the scanning of the ultraviolet ray by means of the stage driving mechanism 503, and it thus becomes possible to observe the state of the localization of the specified components resulting from the fine shape of the surface of the sample over an extremely wide range by means of an image.

In the present embodiment, an example was used in which an XY stage driven by a stepping motor was employed as the stage driving mechanism 503; however, other apparatuses may be employed insofar as they are capable of driving stage 502 in a plane. An example was used in which an CCD line sensor was employed as the plurality of light detectors 303 disposed so as to form a series; however, other apparatuses may be employed insofar as they have a structure in which a plurality of light detectors are disposed so as to form a series. An explanation was conducted using an apparatus in which the fluorescent light detector comprised a spectroscope 301 and a plurality of light detectors 303 disposed so as to form a series; however, the striking effects described in the present embodiment would be realized even in an apparatus having a structure such that the fluorescent light detector comprised a plurality of groups of filters, allowing the transmission of light having specified wavelengths, and detectors. In addition, it is of course the case that the detection sensitivity would be greatly increased if light amplifiers were disposed before each of the plurality of light detectors.

(Embodiment 6)

Figure 13:
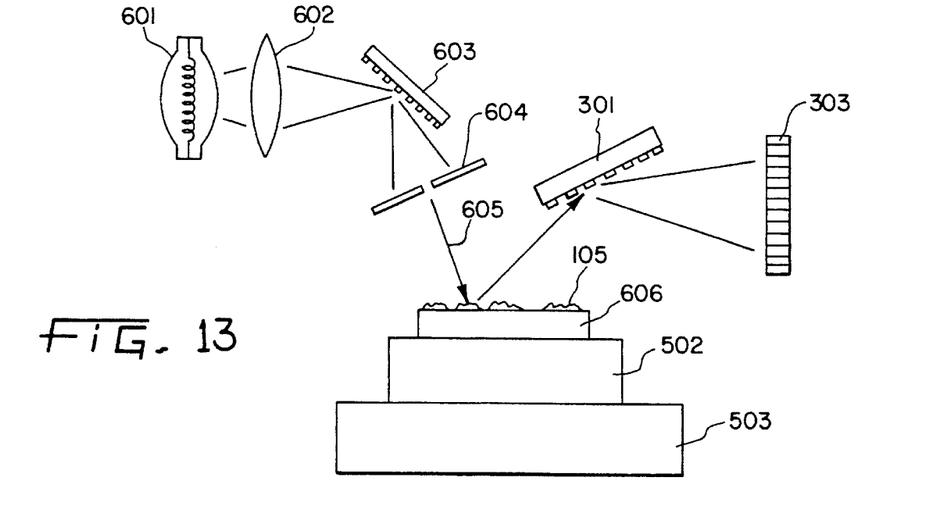
FIG. 13 is a conceptual diagram of an analyzer in accordance with a sixth embodiment.

FIG. 13 shows a sixth embodiment of the present invention. The present embodiment is characterized in that ultraviolet rays emitted by an ultraviolet ray light source 601, for example, a mercury lamp, are collected by a light-gathering instrument 602 comprising, for example, an optical lens, are then inputted into a selector for light having specified wavelengths comprising, for example, a diffraction grating spectroscope 603 and an aperture 604, and only a monochromatic ray 605 having a specified wavelength is applied to sample 606. With respect to the other details of the composition, these are identical to those explained in fifth embodiment, so that an explanation thereof will be omitted here.

As a result of the application of an ultraviolet ray 605 having a single wavelength selected by means of the specified wavelength selector to sample 606, the problem present in the case of a method employing an ultraviolet ray having a single wavelength, that is to say, the undesirable effect (worsening of signal/noise ratio) of stray light during detection of fluorescent light as a result of reflection or irregular reflection, at the surface of the sample, of the visible light component contained in the ultraviolet rays emitted by the ultraviolet ray source, is eliminated, and the detection sensitivity increases dramatically, the signal strength/noise ratio increasing by 50 times, and the like. In addition, by changing the position of the aperture 604 with respect to the spectroscope 603, it is possible to alter the wavelength of the selected ultraviolet ray, and in cases in which the wavelength of fluorescent light emitted by a sample excited by an ultraviolet ray having a specified wavelength is close to the wavelength of the exciting ultraviolet ray, and is thus undetectable, by altering the wavelength of ultraviolet ray which is incidented, the fluorescent light becomes detectable.

Figure 14A:
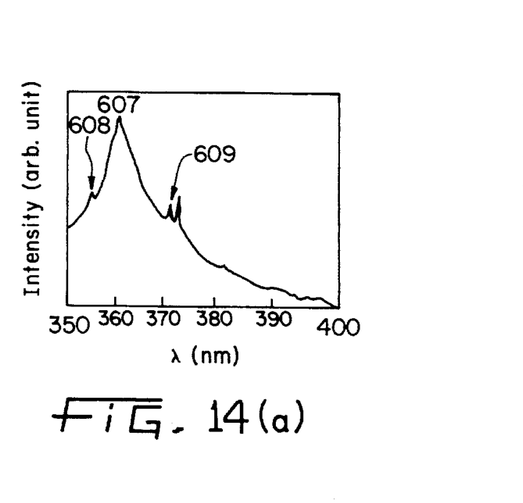
FIG. 14(a) is a diagram showing the state of the measurement of the spectra from 350 nm to 400 nm in an apparatus which is not provided with a specified wavelength selector.

The apparatus will be explained concretely using the diagrams. FIG. 14(a) shows the results of the measurements, in an apparatus which is not provided with a specified wavelength selector, and using a mercury lamp as the ultraviolet ray source, of the spectra of fluorescent light within a wavelength range of 350 nm and 400 nm, using a Si wafer which was deliberately contaminated with the element Fe as a sample. Light having a wavelength of approximately 360 nm was contained in the light emitted from the mercury lamp constituting the ultraviolet ray source, and this light was reflected by the surface of the sample and entered the fluorescent light detector, and as shown by reference 607 in FIG. 14(a), a peak was produced at the point in which the wavelength was 360 nm in the detected spectra of the fluorescent light. As a result of this peak resulting from the reflection of the incidented light, the fluorescent light peaks from the Fe present on the Si wafer (References 608 and 609 in FIG. 14(a)) were obscured, and the accurate analysis of the element Fe became impossible.

Figure 14B:
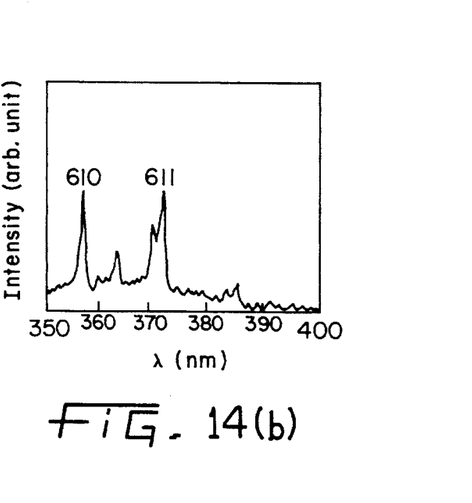
FIG. 14(b) is a diagram showing the state of measurement of the spectra from 350 nm to 400 nm in an apparatus which includes a specified wave length selector.

On the other hand, the spectra obtained in the case in which the same sample was measured using the apparatus of the invention explained in the present embodiment, which was provided with a specified wavelength selector, are shown in FIG. 14(b). As a result of the diffraction grating spectroscope and the aperture, the wavelength of the ultraviolet rays applied to the sample was restricted to 250 nm, and thereby, the detected peak resulted from the incidented light was eliminated, the peaks 610 and 611 of the fluorescent light of Fe can be clearly distinguished, and the lower limit of detection was also $1 \times 10^{10}$ atoms/cm$^2$, in the case in which a light amplifier was not employed.

In the present embodiment, the case in which a mercury lamp was used as the ultraviolet ray light source was explained; however, ultraviolet ray light sources other than mercury lamps, for example, deuterium lamps, may also be employed. An example was used in which an optical lens was employed as a light-gathering instrument 602; however, other apparatuses may be employed in so far as they act as light-gathering instruments, for example, a concave mirror may be employed. The case in which the selector of light having a specified wave length comprised diffraction grating spectroscope 603 and aperture 604 was explained; however, other apparatuses may be employed, insofar as they are able to select a monochromatic ultraviolet ray having a specified wave length, for example, an apparatus comprising a prism and an aperture may be employed. In addition, in the case in which the ray source itself is capable of emitting monochromatic light, for example, in a case in which 1 or a plurality of ekishima lasers having differing excitation wavelengths are used as the light source, it is of course the case that the selector for light having specified wavelengths becomes unnecessary. Furthermore, it goes without saying that by disposing light amplifiers before each of the plurality of light detectors, the detection sensitivity is greatly increased.

(Embodiment 7)

Figure 15:
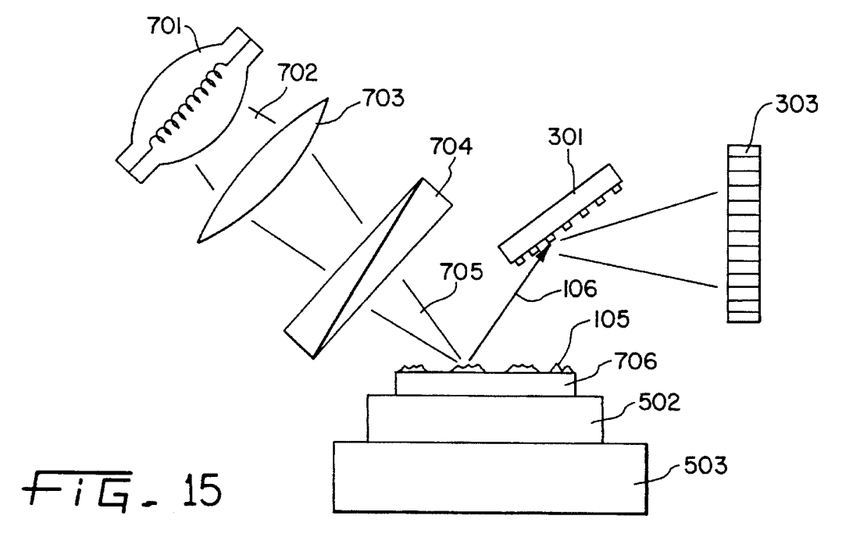
FIG. 15 is a conceptual diagram of an analyzer in accordance with a seventh embodiment.

FIG. 15 shows a seventh embodiment of the present invention. It is characteristic of the present embodiment that the ultraviolet rays 702 emitted by an ultraviolet ray source, for example, mercury lamp 701, are collected by a light-gathering instrument, for example, optical lens 703, these rays are then introduced into a polarizer 704, for example, a Glan prism, having the function of selecting only that component of light having a specified polarization, and then only the singly polarized ultraviolet rays 705 are applied to sample 706, and that by means of moving an ultraviolet ray applying part comprising mercury lamp 701, optical lens 703, and the Glan prism 704, it is possible to alter the angle of incidence of the singly polarized ultraviolet ray 705 with respect to sample 706. With respect to other details of the composition, these are explained in the fifth embodiment, so that an explanation thereof will be omitted here.

When a singly polarized ray is incidented onto a substance, it is well known that by setting the angle of incidence to the angle of polarization which is determined by the index of refraction of the substance, it is possible to produce a state in which there is no reflection. Accordingly, in the apparatus explained in the present embodiment, by incidenting the singly polarized ultraviolet ray 705 selected by the Glan prism 704 onto sample 706 at the angle of polarization, which is set by moving the ultraviolet ray application part, it is possible to produce a state in which there is absolutely no reflected light. By means of completely eliminating reflected light, the signal/noise ratio is increased and the detection sensitivity is greatly increased. Concretely, as a result of conducting the measurement of the fluorescent light spectra of the element Fe in a manner identical to that of the experiment conducted using the apparatus of the sixth embodiment, in contrast to the case in which incidence of the singly polarized ultraviolet ray at the angle of polarization was not conducted, in which the fluorescent light of the element Fe at 358 nm and 372 nm was obscured by means of reflected light and could not be detected, when incidenting of the singly polarized ultraviolet ray at the angle of polarization was conducted, the 2 Fe peaks were observed. In the case in which light amplifiers were not used, the lower limit of detection for Fe was $2 \times 10^{10}$ atoms/cm$^2$.

Furthermore, by incorporating the selector for light having specified wavelengths comprising a diffraction grating in an aperture which was explained in the sixth embodiment into the ultraviolet ray application part, the detection sensitivity is increased, and in the case in which light amplifiers are not employed, the lower limit of detection of Fe is $5 \times 10^9$ atoms/cm$^2$. In the present embodiment, an explanation was given of the case in which Glan prism 704 was employed as the means for obtaining singly polarized light; however, other means may be employed insofar as they are able to obtain singly polarized light. In addition, a mercury lamp was used as the ultraviolet ray light source; however, other apparatuses may be used insofar as they are capable of emitting ultraviolet rays, for example, a deuterium lamp may be employed. In addition, if a laser beam source in which the end surface comprises a Brewster window is employed as the ultraviolet ray light source, the polarizer may be omitted. An example was used in which an optical lens was employed as the light-gathering instrument 703; however, other apparatuses may be employed insofar as they are capable of acting as a light-gathering instrument, for example, a concave mirror may be employed. Furthermore, it is of course the case that if light amplifiers are disposed before each of the plurality of light detectors, the detection sensitivity increases greatly.

We claim:

1. An analyzer for analyzing impurities on the surface of a sample, said analyzer comprising:

a stage for retaining said sample;

a light source for emitting ultraviolet rays;

a means for collecting ultraviolet rays emitted by said light source, and for applying the rays to said surface of said sample; and a means for detecting light emitted by said impurities on said surface of said sample to which said ultraviolet rays were applied, and for determining the wavelength distribution of the detected light.

2. An analyzer in accordance with claim 1, wherein said means for detecting light has the ability to detect light within visible ranges.

3. An analyzer in accordance with claim 2 wherein said means for detecting light includes a spectroscope.

4. An analyzer in accordance with claim 2 including a means for scanning said ultraviolet rays onto said surface of said sample.

5. An analyzer in accordance with claim 2 including a means for scanning said stage.

6. An analyzer in accordance with claim 2 including a means for separating said ultraviolet rays prior to application thereof to said surface of said sample.

7. An analyzer in accordance with claim 1, wherein said means for detecting light includes a spectroscope.

8. An analyzer in accordance with claim 7 including a light amplifier and wherein light separated by said spectroscope is introduced into said light amplifier.

9. An analyzer in accordance with claim 8 including a means for scanning said ultraviolet rays onto said surface of said sample.

10. An analyzer in accordance with claim 8 including a means for scanning said stage.

11. An analyzer in accordance with claim 7 including a plurality of light detectors and wherein said plurality of light detectors simultaneously detect light separated by said spectroscope.

12. An analyzer in accordance with claim 11 including a means for scanning said ultraviolet rays onto said surface of said sample.

13. An analyzer in accordance with claim 11 including a means for scanning said stage.

14. An analyzer in accordance with claim 7 including a means for scanning said ultraviolet rays onto said surface of said sample.

15. An analyzer in accordance with claim 7 including a means for scanning said stage.

16. An analyzer in accordance with claim 7, including a means for separating said ultraviolet rays prior to application thereof to said surface of said sample.

17. An analyzer in accordance with claim 1 including a means for scanning said ultraviolet rays onto said surface of said sample.

18. An analyzer in accordance with claim 1 including a means for scanning said stage.

19. An analyzer in accordance with claim 1 wherein a means for separating said ultraviolet rays prior to application thereof to said surface of said sample is provided.

* * * * *